United States Patent [19]

Hartwick

[11] 4,191,649

[45] Mar. 4, 1980

[54] LIQUID CHROMATOGRAPHY SYSTEM WITH SIMULATED GRADIENT

[76] Inventor: Richard A. Hartwick, Old Mine Rd., Layton, N.J. 07851

[21] Appl. No.: 953,699

[22] Filed: Oct. 23, 1978

[51] Int. Cl.² ............................................. B01D 15/08
[52] U.S. Cl. ................................. 210/198 C; 73/61.1 C
[58] Field of Search ................. 210/198 C; 73/61.1 C

[56] References Cited

U.S. PATENT DOCUMENTS

| | | | |
|---|---|---|---|
| 4,003,243 | 1/1977 | Blu et al. | 210/198 C |
| 4,032,445 | 6/1977 | Munk | 210/198 C |
| 4,063,077 | 12/1977 | Wright | 210/198 C |
| 4,073,725 | 2/1978 | Takeuchi et al. | 210/198 C |

Primary Examiner—John Adee
Attorney, Agent, or Firm—Barlow & Barlow

[57] ABSTRACT

In a liquid chromatography system a secondary pumping system is disclosed which produces a simulated mobile phase gradient that may be pumped through a reference cell at atmospheric pressure. The secondary pumping system is connected to the primary pumping system so as to maintain the flow at the same rate as in the primary pumping system.

4 Claims, 2 Drawing Figures

LIQUID CHROMATOGRAPHY SYSTEM WITH SIMULATED GRADIENT

BACKGROUND OF THE INVENTION

This invention is directed towards liquid chromatography utilizing gradient elution which actually is the changing of the chemical composition of the mobile phase or the eluent as a function of time which improves the performance of the chromatography system especially when one has samples that contain components which vary widely in chemical properties. The usual arrangement for this type of device is shown, for example, in the prior art as in U.S. Pat. No. 4,032,445 and in the literature, for example, in L. R. Snyder and J. J. Kirkland, "Introduction To Modern Liquid Chromatography," Wiley & Sons, N.Y. 1978, page 115.

A problem arises as the use of gradient elution for the changing eluent composition can produce a signal of its own, and when this occurs, the detector will yield a base line which may rise inasmuch as the gradient produces a detector response of its own. When a base line becomes non linear a detection in quantitative analysis is difficult or next to impossible in many situations.

Some attempts in the past have been made to correct the problem by splitting the high pressure flow line leading into the column and diverting part of the flow through the reference cell. It is difficult, however, to equalize the flow that is diverted into a reference cell to that in the main high pressure sample cell. One of the reasons behind this is that it is almost impossible to produce two columns which give exactly equal pressure drops, and this is an absolute necessity since variation in pressure will produce flow rate variations and in turn variations in retention times. Secondly, even if such an approach were feasible, column expense would be a major deterrent as columns are rather costly and have a limited lifetime.

SUMMARY OF THE INVENTION

The invention is an approach to solving the problem of base line compensation in a liquid chromatography apparatus system using gradient elution. To provide for simulating the gradient being produced in the main pumping system a set of slave or secondary pumps are driven prefereably by the main or primary pumps and may be mechanically or electronically couple thereto. The secondary pumps derive their source of eluent from the same source as the primary pumps, and the output passes through a suitable delay device or volume compensator which can be nothing more than suitably treated tubing. The arrangement proposed herein is adaptable to many existing structures as well as being adaptable to new designs. Most liquid chromagraphs of current design employ any of several types of reciprocating pumps, and the mobile phase composition is varied by varying the relative frequency of the pumps while maintaining a constant overall flow rate. By coupling the secondary pumps to the primary pumps, the secondary pumps will produce exactly the same mobile phase composition as the primary pumps. However, since the secondary pumping system is completely separate from the primary system, the eluent of the secondary system can be passed through a reference cell at atmospheric pressure. cl DESCRIPTION OF THE DRAWINGS FIG. 1 is a diagrammatic view of a chromatograph embodying the principles of the invention;

FIG. 2 is a detached view partially diagrammatic and partly in section illustrating one means of adapting a pump to an existing pump.

DESCRIPTION OF THE PREFERRED EMBODIMENT

Figure 1:
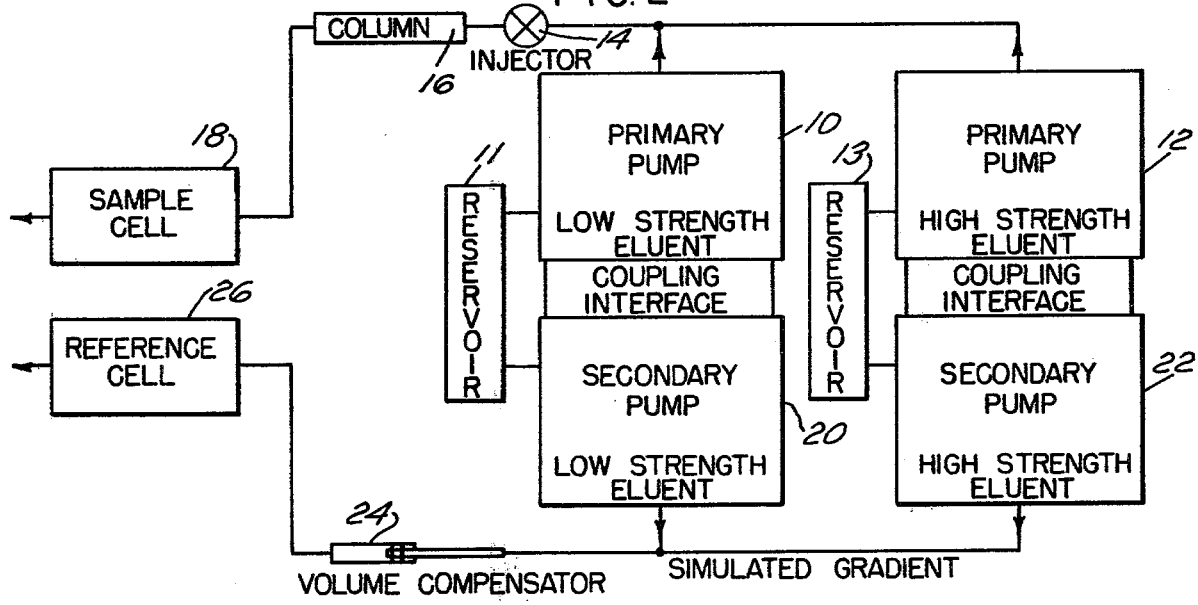

In reference to the drawing in FIG. 1, there is disclosed a primary pump 10 that is fed from a source of low strength eluent in a reservoir 11 and a second primary pump 12 fed from a second source of high strength eluent in a second reservoir 13. The outputs of the two pumps 10 and 12 are combined through an injector 14 to a column 16 and thence to the primary sample cell 18. The system just described is quite common, it being understood that the sample is usually introduced at injector 14, and as the sample liquid elutes from the column 16, it may be viewed with a variety of devices in the cell 18 which usually encompass the utilization of a detector that monitors a change in the absorbance or other property of the sample liquid. The above system is effective when one has a difficult separation to detect where gradient elution is utilized and a second pump continuously introduces another eluent or high strength solvent at a continuously changing rate.

To avoid a problem where the eluent changes and accordingly the zero or base line will change during gradient elution, a set of slave or secondary pumps 20 and 22 are coupled to the reservoirs containing the two strength eluents. Mechanically or electronically the pumps are coupled to the primary pumps 10 and 12 so that they will keep pace therewith and as the eluent compositions change by virtue of the primary pumps actions, the secondary pumps will follow these changes. For example, it is very common to vary the mobile phase composition by varying the relative frequency of pumping of each pump. Accordingly, this same variation will take place in the secondary pumps 20 and 22 as in the primary pumps 10 and 12 due to the coupling interface. The output of the secondary pumps 20 and 22 which contain the simulated gradient are directed to what is termed a volume compensator 24, and thence to a reference cell 26 which is physically placed adjacent the sample cell 18 so that it may be viewed by the same detection system.

It has been mentioned that it is necessary that the simulated gradient or the mobile phase of the given composition must reach the reference cell 26 at the same time and with the same composition as that that is being placed through the main system fed by the primary pumps. Accordingly, the void volumes of both the primary and secondary systems must match in terms of time rather than volume. The equation that must be satisfied, therefore, is that the volume of the primary system divided by the flow rate of the primary system must be equal to the volume of the secondary system divided by the flow rate of the secondary system. Accordingly, if the primary system is designed to have a flow rate of 1.0ml/min and the secondary system has a flow rate of 0.1ml/min, a void volume of the secondary system must be equal to 0.1 times the void volume of the main system. To achieve this, the volume compensator 24 has been diagrammed and may consist simply of a variable volume coupling to perform exact calibration.

Figure 2:
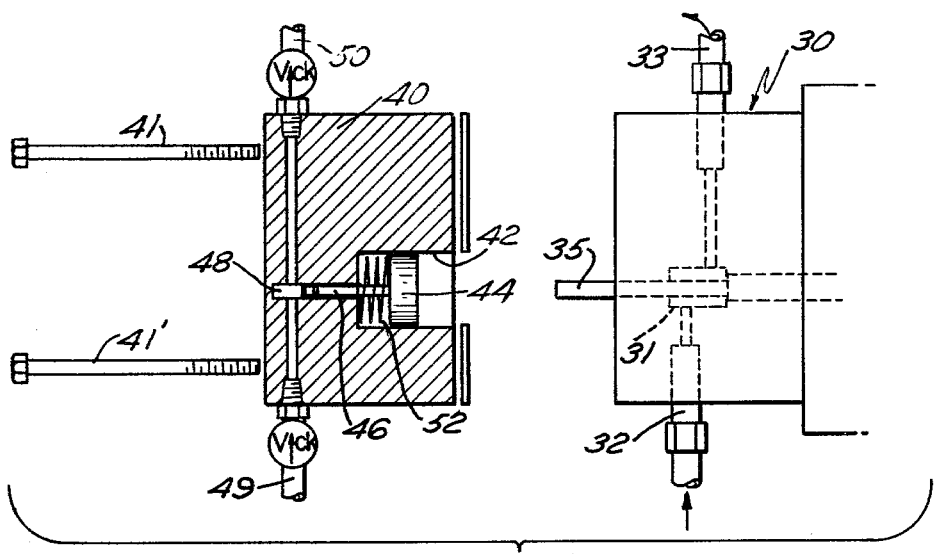

Referring now to FIG. 2 in the drawings, there is shown one possible approach of the modifying of existing apparatus so that it will perform in accordance with the invention. Generally designated 30 is a pump arrangement that is manufactured in accordance with U.S. Pat. No. 3,855,129 which has a pumping chamber 31 with inlet and outlet means 32, 33 respectively. Within the pumping chamber there is located a plunger which has affixed to the end thereof an indicator rod 35 that extends from the body of the pump. This indicator rod operates with the main pumping plunger and therefore an auxiliary or secondary pump having a body 40 can be clamped onto the pumping body 30 by the use of bolts 41, 41' or any other suitable attaching device. The secondary pump 40 in this case may be provided with a cylindrical recess 42 into which is fitted a cylinder 44 for reciprocation therein. Extending from the cylinder 44 is a pumping piston 46 that reciprocates in a pumping chamber 48. As is usual in pumping structures, there is provided an inlet 49 and an outlet 50 with suitable check valves therein and it will be apparent to those skilled in the art that reciprocation of the piston 46 will draw liquid therein and force it out.

When the secondary pump 40 is affixed to the main pump 30, the indicator rod 35 will abut the cylinder 44, and inasmuch as the cylinder 44 is urged against the rod 35 by a spring 52, there will be actuation of the secondary pumping piston 46 on every stroke of the main pumping piston.

It should be apparent that this is just one possible manner in which a secondary pump can be fitted to an existing device and it is intended to be illustrative rather than limiting. As understood by those skilled in the art, the instant invention has disclosed the utilization of a primary or high pressure pumping system in combination with a secondary low pressure pumping system for liquid chromatography. It can be structurally realized by the addition of a small low pressure secondary pump to an existing primary high pressure pump and synchronizing the same thereto in a manner so that the secondary pumping system that creates an exact reproduction of the gradient being produced in the primary system.

What is claimed is:

1. In a liquid chromatography system having a first and second reservoirs for eluent with first and second pumps connected thereto and a first conduit, the discharge of the pumps connected thereto, said conduit connected to a column and sample cell in series, that improvement comprising providing a reference cell, third and fourth pumps, said third and fourth pumps connected to the first and second reservoirs and discharging into a common second conduit, said common second conduit connected to a volume compensator and said reference cell in series, said third and fourth pumps driven in unison with said first and second pumps.

2. A system as defined in claim 1 wherein said third and fourth pumps are mechanically connected to said first and second pumps.

3. A system as defined in claim 1 wherein said second conduit includes a volume compensator to reproduce the volume of said first conduit.

4. A system as defined in claim 1 wherein said reference cell and said sample cell are placed adjacent each other.

* * * * *